United States Patent
Jonsson Axelsson et al.

(10) Patent No.: US 9,945,810 B2
(45) Date of Patent: Apr. 17, 2018

(54) INTEGRATED SYSTEM FOR ELECTRO-BLOTTING

(71) Applicant: GE Healthcare Bio-Sciences AB, Uppsala (SE)

(72) Inventors: Urban Jonsson Axelsson, Uppsala (SE); Lars Erik Hammarstrand, Uppsala (SE); Girish Kittur, Bangalore (IN); Shekar Ambepu, Bangalore (IN); Bharath Subrahmanya, Bangalore (IN); Mahesh Bhat, Bangalore (IN); Kalyana Chakravarthy Duggirala, Bangalore (IN)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 71 days.

(21) Appl. No.: 15/038,976

(22) PCT Filed: Nov. 21, 2014

(86) PCT No.: PCT/EP2014/075269
§ 371 (c)(1),
(2) Date: May 24, 2016

(87) PCT Pub. No.: WO2015/078781
PCT Pub. Date: Jun. 4, 2015

(65) Prior Publication Data
US 2016/0377574 A1    Dec. 29, 2016

(30) Foreign Application Priority Data
Nov. 29, 2013 (IN) .......................... 3479/DEL/2013

(51) Int. Cl.
*G01N 27/447* (2006.01)

(52) U.S. Cl.
CPC ............... *G01N 27/44739* (2013.01)

(58) Field of Classification Search
CPC ....... G01N 27/44773; G01N 27/44704; G01N 27/44782; G01N 27/44739
See application file for complete search history.

(56) References Cited

U.S. PATENT DOCUMENTS
2005/0186641 A1    8/2005 Haugland et al.

FOREIGN PATENT DOCUMENTS

| EP | 1411358 A1 | 4/2004 |
|---|---|---|
| WO | 93/03359 A1 | 2/1993 |
| WO | 02/48674 A2 | 6/2002 |

OTHER PUBLICATIONS

International Search Report and Written Opinion regarding International Application No. PCT/EP2014/075269, dated Feb. 2, 2015, 11 pages.

*Primary Examiner* — J. Christopher Ball
(74) *Attorney, Agent, or Firm* — Eversheds Sutherland (US) LLP

(57) ABSTRACT

An integrated system for performing electro-blotting, probing and drying of the membrane is disclosed. The integrated system comprises a transfer unit for receiving one or more transfer sandwich holder. Each transfer sandwich holder holding a transfer sandwich comprises a gel member and the membrane. The transfer unit is configured to transfer samples from the gel member to the membrane. The integrated system also includes a probing unit for receiving the membrane therewithin. The membrane is exposed to a plurality of antibodies for binding with the samples in the membrane. A drying unit is also present for drying the membrane with hot air.

22 Claims, 13 Drawing Sheets

INTEGRATED SYSTEM FOR ELECTRO-BLOTTING

CROSS-REFERENCE TO RELATED APPLICATIONS

This application is a filing under 35 U.S.C. 371 of international application number PCT/EP2014/075269, filed Nov. 21, 2014, which claims priority to Indian application number 3479/DEL/2013, filed Nov. 29, 2013, the entire disclosures of each of which are hereby incorporated by reference.

FIELD OF THE INVENTION

The subject matter disclosed herein relates to electro-blotting of samples such as proteins, probing and drying and more particularly to a device for performing the probing of membrane holding the samples and drying the probed membrane.

BACKGROUND OF THE INVENTION

Electrophoresis is an analysis method commonly used that involves migration of charged molecules and particles in a separation medium, usually a gel, when subjected to electrical field between two electrodes. Separation of molecules and particles such as proteins may be by isoelectric point (pI), molecular weight, electric charge, or a combination of these factors. The separation medium is usually placed on a support and two opposing ends of the medium are contacted with an electrode buffer in solution or rigid thrift. The electrodes may be inserted in vessels containing the electrode buffers. The buffer solutions from both the electrolytic medium and a reservoir for ions to keep the pH and other parameters constant. After separation, the molecules are detected and identified in different ways: e.g. visually by staining the gel or by optical means such as scanning or imaging the stained gel or labeller samples by a laser scanner or the like.

Electrophoresis process using gel is commonly used for separating biomolecules such as proteins, peptides, nucleic acids etc. Samples are handled in different types of screening, identifying (cell signaling, expression & purification) or in clinical tests. Protein samples can derivate from e.g. human, mammalian tissue, cell lysates or bacterial, insect or yeast cellular systems. The electrophoretic conditions for different types of molecules are different and have to be adapted in many cases. Thus, both the gel and the buffer solutions must often be chosen for each type of sample.

The preparation of the electrophoresis process includes several rather laborious steps. A suitable gel is chosen and placed or molded on a support. The gel is contacted with the buffer solutions. A common way is to have a gel slab in a cassette of glass or plastic in contact with the buffer solutions in buffer tanks. For each run the gel has to be placed on the support or the cassette to be prepared. Then the buffer tanks are filled with buffer solutions and the samples are applied on the gel. To go away from the handling of buffer solutions in buffer tanks it has been suggested, in WO 87/04948, to incorporate the buffer substance in a gel material whereby the buffer is obtained in the form of a buffer strip. In addition U.S. Pat. No. 6,368,481 discloses a precast electrophoresis cassette wherein buffer strips are incorporated as an integral part of the cassette.

Following the electrophoretic separation and in order to detect specific proteins in a given sample, the proteins may be transferred to a membrane (typically nitrocellulose or PVDF), where they are probed (detected) using antibodies specific to the target protein, a process commonly referred to as western blotting or immunoblotting. The primary method for transferring the proteins to the membrane is referred to as electroblotting and uses an electric current to pull proteins from the gel into the membrane. The proteins move from within the gel onto the membrane while maintaining the organization they had within the gel, whereby the proteins are exposed on a thin surface layer for detection. The proteins bind to the surface of the membrane due to its non-specific protein binding properties (i.e. binds all proteins equally well). In order to avoid unspecific binding of probing antibodies, remaining binding sites on the membrane may be blocked. During the probing (detection) process the membrane with the transferred proteins is incubated with specific primary antibody directed towards the protein of interest and secondary antibody e.g. for the protein of interest with a modified antibody which is linked to a reporter enzyme; when exposed to an appropriate substrate this enzyme drives a colorimetric reaction and produces a colour or by fluorescently labeled targets (dyes), that may be detected by a suitable imaging technique after drying.

All the steps involved in electrophoretic separation, probing and drying of the membrane containing the proteins are performed manually and also in different equipments. As different equipments are being used a technician needs to manually transfer the transfer sandwich or membrane from one equipment to another. So the likelihood of the membrane getting damaged is more. Now for drying the membrane, this needs to be done by placing the membrane in a location and air is supplied using a fan. Manual handling during the drying process also causes damage to the membrane as well as delay to whole analysis process. Moreover any damage to the membrane may result in inaccurate analysis of detection of different proteins.

Therefore there is a need for an improved system for performing electro-blotting electrophoretic separation, probing and drying of the membrane prior to detection of proteins in the membrane.

SUMMARY OF IRE INVENTION

The object of the invention is to provide an improved system for performing electro-blotting, probing and drying of the membrane, which overcomes one or more drawbacks of the prior art. This is achieved by an integrated system for performing electro-blotting, probing and drying of membrane holding samples i.e. proteins as defined in the independent claim.

One advantage with the disclosed integrated system is a single system that can be used to perform the process of electro-blotting, probing and drying of the membrane to prepare for analyzing the samples.

According to an embodiment there is provided an integrated system for performing electro-blotting, probing and drying of the membrane is disclosed. The integrated system comprises a transfer unit for receiving one or more transfer sandwich holder. Each transfer sandwich holder holding a transfer sandwich comprises a gel member and the membrane. The transfer unit is configured to transfer samples from the gel member to the membrane. The integrated system also includes a probing unit for receiving the membrane therewithin. The membrane is exposed to a plurality of antibodies for binding with the samples in the membrane. A drying unit is also present for drying the membrane with hot air.

According to one embodiment the integrated system comprises a modules holder comprising a transfer compartment for holding the transfer unit, a probing compartment for holding the probing unit, and a dryer compartment holding the drying unit.

According to one embodiment the transfer unit comprises one or more sandwich slots for holding a transfer sandwich holder of the one or more sandwich holder; and a plurality of electrodes for facilitating the transfer of samples from the gel member to the membrane in presence of a transfer buffer.

According to one embodiment an electrode of the plurality of electrodes comprises a connector for arranging the electrode within a respective electrode slots of transfer unit; and one or more wire wound around the electrode.

According to one embodiment the probing unit comprises an agitation unit for holding the membrane and capable of performing agitation operation for interacting the plurality of antibodies with samples in the membrane; and a supply unit for supplying the plurality of antibodies into the agitation unit. In one embodiment the agitation unit is arranged to process two or more membranes in parallel.

According to one embodiment the agitation unit comprises an agitation platform having the membrane placed thereon and receiving the plurality of antibodies therewithin; and platform maneuvering assembly operatively connected to the agitation platform, wherein the platform maneuvering assembly comprises a connecting rod operatively connected to a bottom portion of the agitation platform; a crank connected to the connecting rod; and a motor assembly connected to the crank. The motor assembly operates rotate the crank thereby moving the connecting rod for facilitating agitation movements of the agitation platform, wherein the agitation movements assist interaction of the plurality of antibodies with the membrane.

According to one embodiment the integrated system comprises a base unit. The agitation platform is pivotally mounted on the base unit to facilitate the agitation movements.

According to one embodiment the integrated system comprises a plurality of storage units and a fluid pump system. One or more storage units comprise washing fluids. The fluid pump system for delivering washing and blocking fluid into the agitation platform the washing the membrane.

According to one embodiment the integrated system comprises a plurality of supply tubes and a plurality of tube holders. A supply tube connects a storage unit of the plurality of storage units to the fluid pump system. A tube holder is clamped to the supply tube for holding the supply tube in a predefined position.

According to one embodiment the integrated system comprises a drying unit. The drying unit comprises one or more membrane holders arranged within drying chamber. A membrane holder having one or more slots is configured to hold the membrane contacting two end portions of the membrane within the drying member. The drying unit also includes an hot air supply unit for supplying hot air along the membrane for drying.

A more complete understanding of the present invention, as well as further features and advantages thereof will be obtained by reference to the following detailed description and drawings.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of the invention including an integrated system for performing electro-blotting, probing and drying of the membrane is disclosed. The integrated system comprises a transfer unit for receiving one or more transfer sandwich holder. Each transfer sandwich holder holding a transfer sandwich comprising a gel member and the membrane. The transfer unit is configured to transfer samples from the gel member to the membrane. The integrated system also includes a probing unit for receiving the membrane therewithin. The membrane is exposed to a plurality of antibodies for binding with the samples in the membrane. A drying unit is also present for drying the membrane with hot air.

Figure 1:
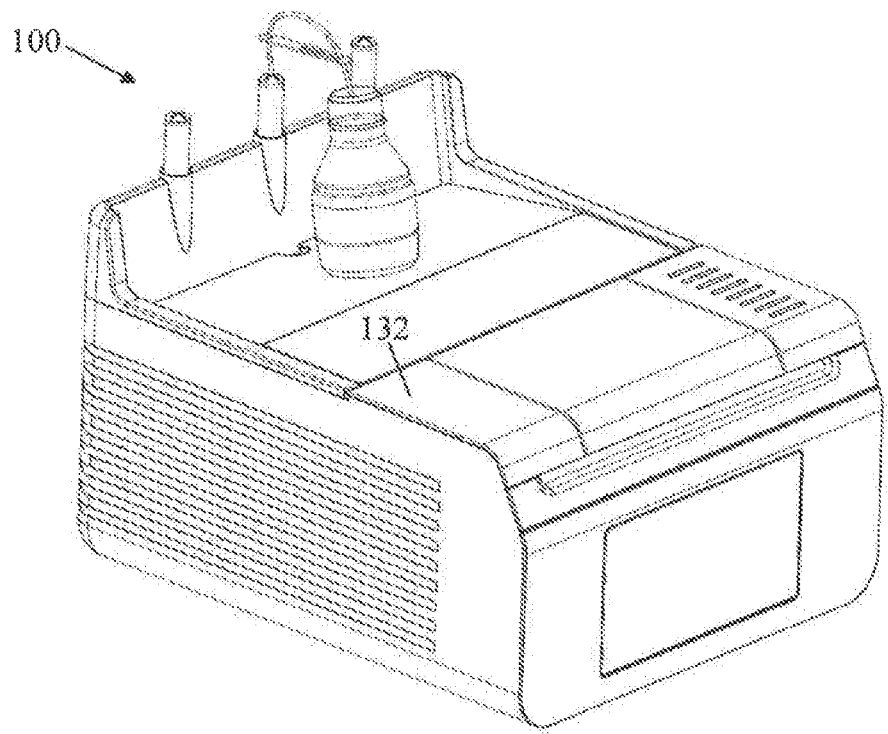
FIG. 1 is a schematic perspective view of an integrated system for electro-blotting, blotting and drying in accordance with an embodiment.
Figure 2:
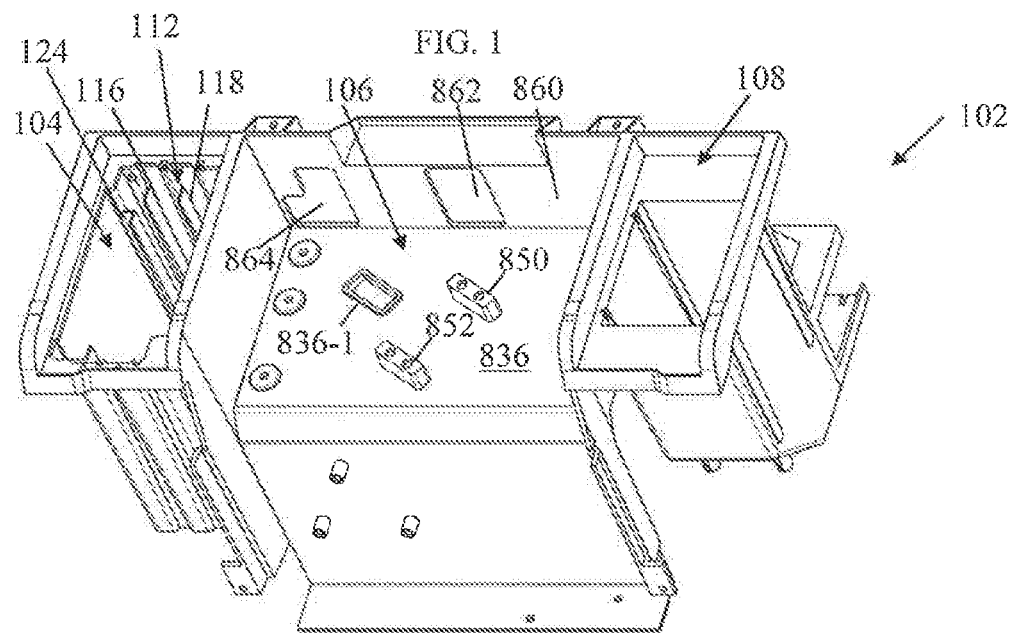
FIGS. 2 and 3 is a schematic illustration of a modules holder in accordance with an embodiment.
Figure 3:
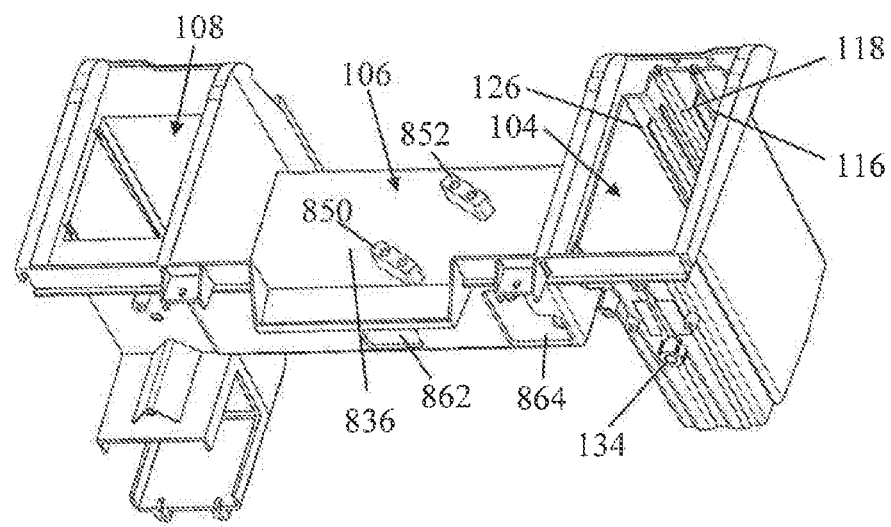
Figure 4:
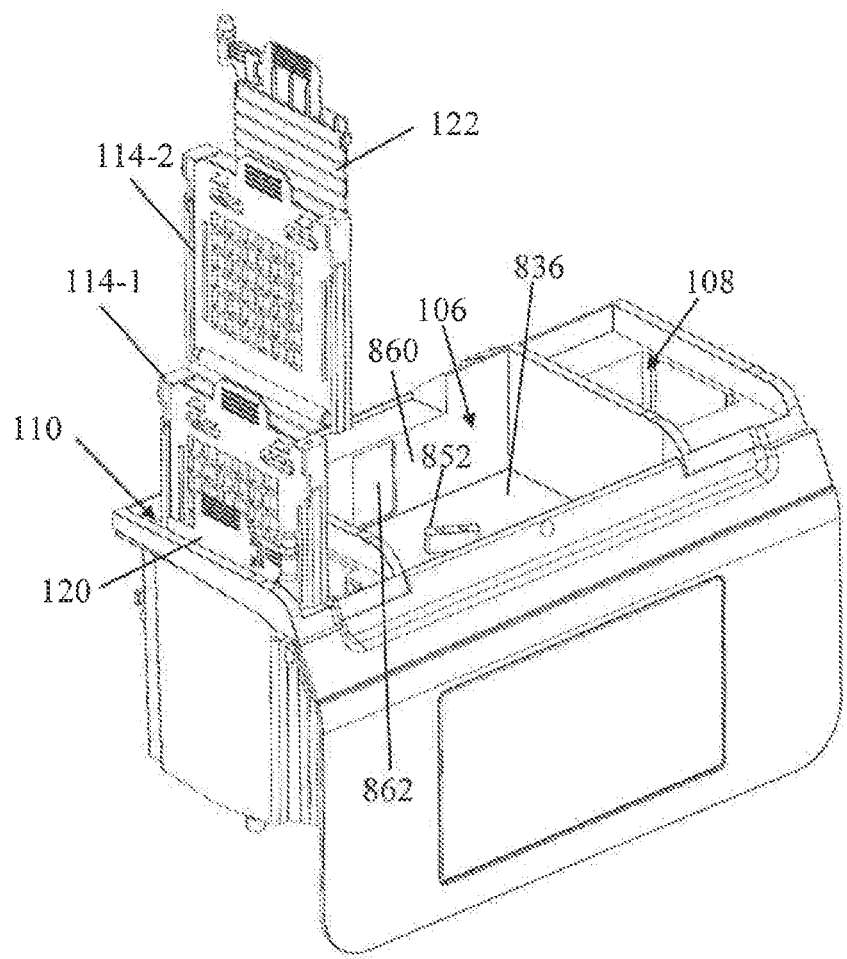
FIG. 4 is a schematic illustration of a exploded view of a transfer unit in the modules holder in accordance with an embodiment.
Figure 5:
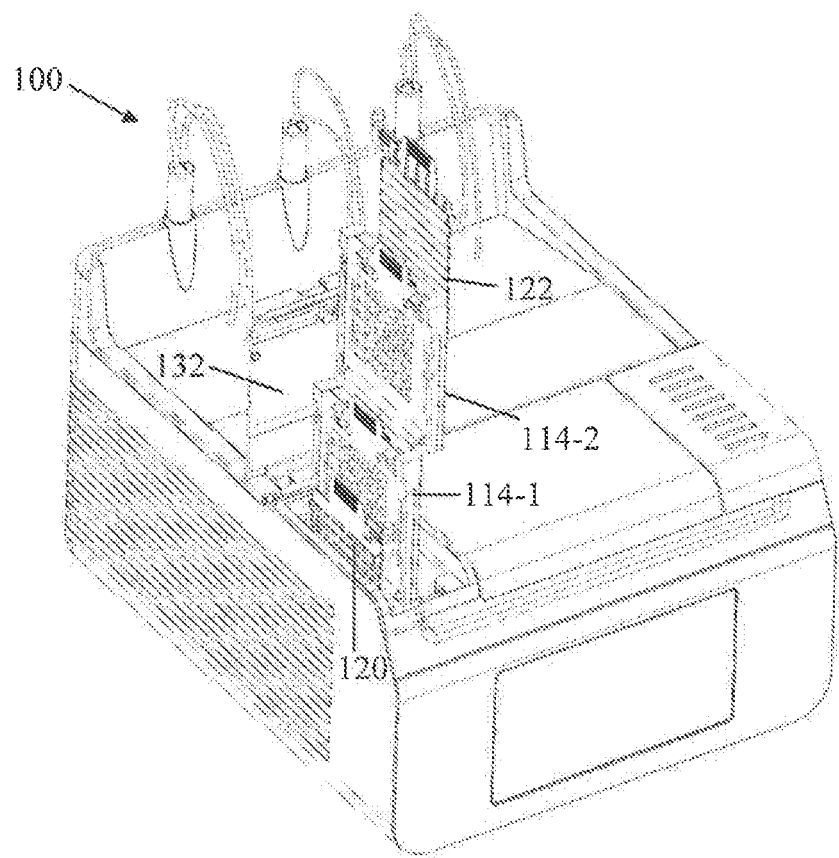
FIG. 5 is a schematic illustration of a exploded view of a transfer unit in the modules holder of the integrated system in accordance with an embodiment.

FIG. 1 is a schematic perspective view of an integrated system 100 for electro-blotting electrophoretic separation, blotting and drying in accordance with an embodiment. The integrated system 100 is a single device that embodies multiple units for performing electro-blotting of samples (i.e. proteins) from a gel member to a membrane, blotting of the membrane holding the proteins and drying the membrane after the blotting process. In electro-blotting a transfer sandwich holder holding a transfer sandwich is used. The transfer sandwich includes sponge members, filters, a gel member, and a membrane. The transfer sandwich holder is placed between two electrodes in presence of a transfer buffer to perform the electro-blotting. The membrane holding the samples (i.e. proteins) needs to be probed with antibodies so that antibodies can bind to some of the proteins of interest. The probed membrane may be in a wet condition and need to be dried. The probed membrane is then diagnosed using an imaging device to detect the proteins of interest. The integrated system 100 enables a technician to perform all these processes of electro-blotting in a single device making it convenient for usage. The integrated system 100 requires very minimal manual intervention and the output is more quantitative & qualitative & repeatable as compared to others prior art processes. In the present system, skill or the workmanship of the user is minimised to get more accurate results The integrated system 100 includes a modules holder 102 having a transfer compartment 104, a probing compartment 106 and a dryer compartment 108 as shown in FIG. 2 and FIG. 3 in accordance with an embodiment. The modules holder 102 may be composed of plastic material. The modules holder 102 may be made using a plastic molding technique. It may be appreciated that the modules holder 102 may be composed of different materials other than plastic and accordingly the different techniques may be used to fabricate or mold the modules holder 102. The transfer compartment 104 includes a transfer unit 110 for receiving one or more transfer sandwich holders as shown in FIG. 4. The transfer unit 110 comprises one or more sandwich slots such as a sandwich slot 112. The sandwich slot 112 is used for holding a transfer sandwich holder 114-1 and a transfer sandwich holder 114-2 in place within the transfer compartment 104. The sandwich slot 112 may have a structure including multiple guide ways or tracks 116 and 118 enabling the transfer sandwich holder 114-1 to slide through and get seated within the transfer compartment 104. The transfer unit 110 is shown in FIG. 4 and FIG. 5 to hold two transfer sandwich holders as an exemplary embodiment however it may be envisioned that a transfer unit may have a configuration to hold only one or more than two transfer sandwich holders. In an embodiment a sandwich slot i.e. the sandwich slot 112 may be an integral part of the transfer compartment 104. In an embodiment the transfer compartment 104 along with the transfer unit 110 having the sandwich slot 112 may a single structure i.e. a molded portion of the modules holder 102. In another embodiment the transfer unit 110 having the sandwich slot 112 may be a separate unit (these are not shown separately in FIG. 2 and FIG. 3) which may be inserted and configured within the transfer compartment 104. In this embodiment only the transfer compartment may be a molded portion of the modules holder 102. Even though only these structural embodiments of the transfer compartment 104 are discussed in detail above, it may be envisioned that the other structural variations in a transfer compartment are possible and these variations are within the scope of this disclosure.

The transfer compartment 104 may also include multiple fastening units for securely holding the transfer sandwich holders 114-1 and 114-2 in the sandwich slot 112. In an embodiment a fastening unit may be a poke-yoke keying unit (not shown in FIGS. 2, 3 and 4). This ensures that the transfer sandwich holders 114-1 and 114-2 to place the holder in correct orientation. Keying helps in placing the transfer sandwich holders 114-1 and 114-2 placed in one direction only. This helps in avoiding confusion in the user as to which side of the holder come which side of the electrode. But as you mentioned keying do not actually avoid holders to come out of the compartment. The sandwich holders has to be removed once the transfer operation is completed It may be also envisioned that other fastening units may be used for holding the transfer sandwich holders 114-1 and 114-2 in the sandwich slot 112.

To perform electro-blotting process multiple electrodes are required, and hence the transfer unit 110 includes two electrodes i.e. a first electrode 120 and a second electrode 122. The first electrode 120 is placed within the transfer unit 110 by inserting into a slot 124 and the second electrode 122 is inserted into a slot 126. The slot 124 and slot 126 are configured within the transfer compartment 104. The first electrode 120 may be connected to a negative terminal and the second electrode 122 may be connected to the positive terminal. The electrodes can shift their positions i.e. the first electrode 120 can be seated in the slot 126 and connected to a negative terminal and the second electrode 122 can be seated in the slot 124 and connected to a positive terminal. Thus if the technician places these electrodes 120 and 122 with their positions changed even then the electrodes will work for performing the electro-blotting process. So based on the terminal (negative or positive) to which the electrodes 120 and 122 are connected the electrodes may be designated as a positive electrode and a negative electrode. In an embodiment the electrodes 120 and 122 may be plugged onto plugs provided in the transfer compartment 104. The electrodes such as an electrode 120 are explained in detail in conjunction with FIG. 6 and FIG. 7. Once the transfer sandwich holder 114 and the electrodes 120 and 122 are placed within the transfer compartment 104 then a transfer buffer is supplied into the compartment. The transfer compartment 104 may have a capacity of 1 liter. It may be appreciated that the transfer compartment may have different capacity based on the requirements of the electrophoretic process. Electric current is supplied through the electrodes 120 and 122 so that electro-blotting process starts to facilitate the transfer of proteins from the gel member to the membrane. The method of supplying the transfer buffer into the transfer compartment 104 is described in detail in conjunction with FIG. 19. Multiple transfer sandwich holders may be placed within the transfer compartment 104 and the electro-blotting process may be performed simultaneously to enable the transfer of proteins from the gel member to the membrane. The transfer compartment 104 also includes a lid 132 for opening and closing this compartment. The electrophoretic process is performed after closing the lid 132.

The transfer compartment 104 also includes multiple inlets and outlets for connecting different pumping systems. These pumping systems may be capable of supplying the transfer buffer into the transfer compartment 104 and draining out the transfer buffer after use. The transfer compartment 104 may include a filter for filtering the transfer buffer pumped into the compartment. The filter may be positioned at an end of an opening 134 (shown in FIG. 3) through which the transfer buffer enters the transfer compartment 104. In an embodiment the opening 134 may be provided with more than one filter. The transfer compartment 104 may include one or more sensors for sensing a level of transfer buffer present in the compartment. Once the sensor detects that the transfer buffer is filled to a predefined level the flow of transfer buffer into the transfer compartment 104 is stopped. Thus the sensor controls the flow of the transfer buffer into the transfer compartment 104. The sensor may be also capable of detecting that the level of transfer buffer is fallen beyond a predefined level and in response supply of the transfer buffer into the transfer compartment 104 is started. More specifically if the sensor detects that the transfer buffer is filled and reaches the predefined level then the supply of the transfer buffer is stopped. If the sensor detects that the level of the transfer buffer has fallen beyond the predefined level then the supply of the transfer buffer is initiated. Few sensors may be also present to detect if the transfer buffer level has reached different levels and accordingly modifying the supply of the transfer buffer into the transfer compartment 104. Moreover there may be sensors present in the transfer compartment to detect opening and closing of the lid 132. Also sensors may be available to detect the presence of the transfer sandwich holder 114 in the transfer compartment 104.

Figure 6:
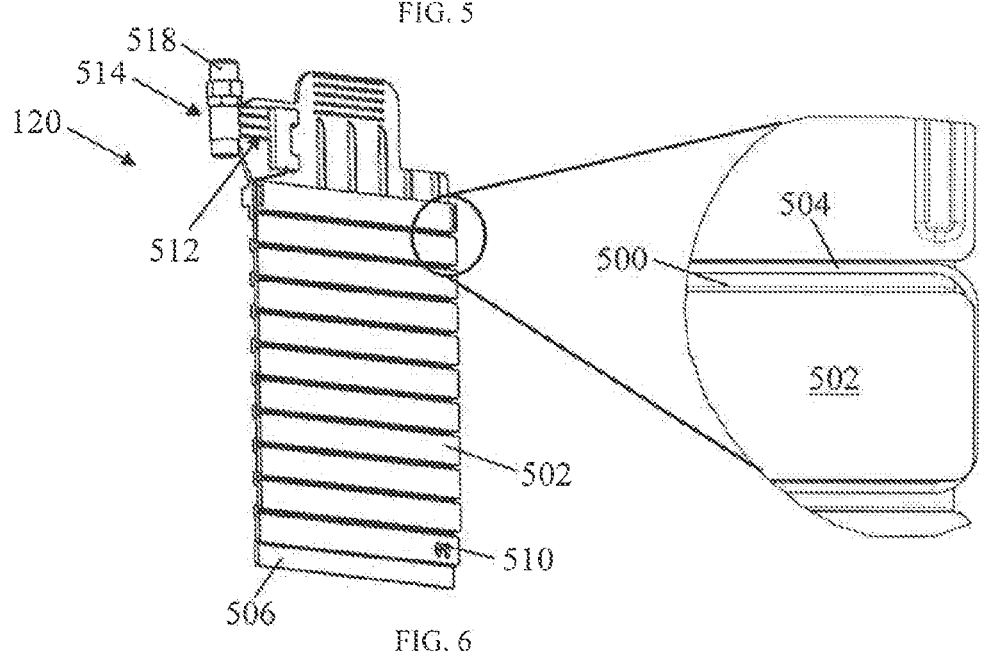
FIGS. 6 and 7 are a schematic illustration of a perspective view and side view of an electrode used in the integrated system in accordance with an embodiment.
Figure 7:
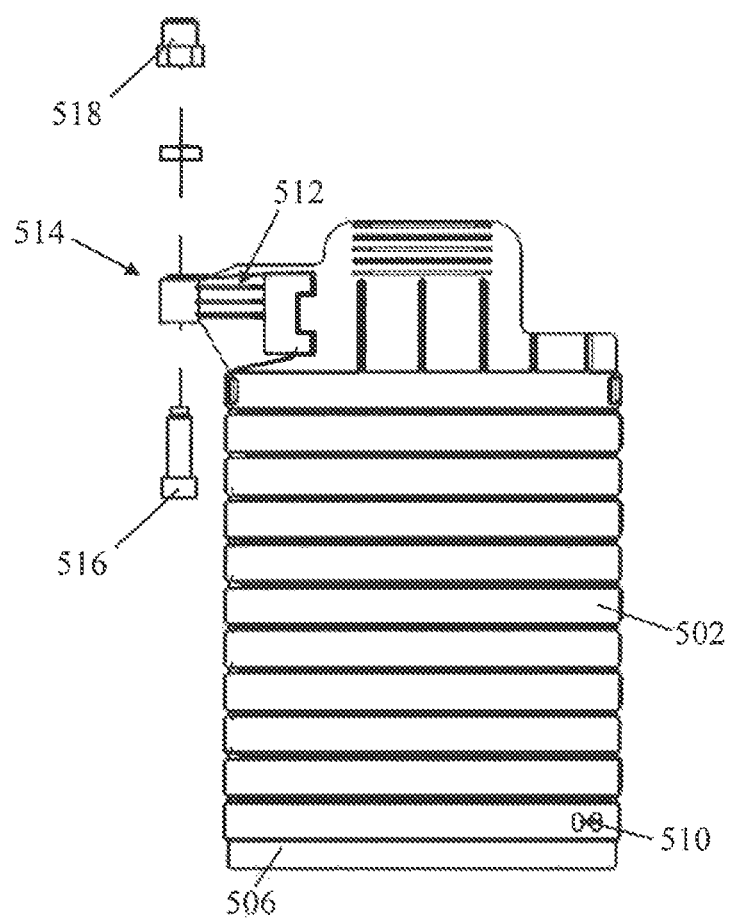

FIG. 6 and FIG. 7 illustrate a perspective view and a side view of the first electrode 120 used in a transfer compartment 104 in accordance with an embodiment. The first electrode 120 may be made of a plastic material. For example the first electrode 120 may be composed of a polymer plastic material such as polyquinoline, polyphenylquinoxaline, polycarbazole, polypyridine, polypyrrole, polyaniline or crystal01upolyindole or any other nitrogen-containing conductive polymer. It may be appreciated that in other embodiments the electrodes for example the first electrode 120 and the second electrode 122 may be composed of any other conductive plastic material. The first electrode 120 includes a threaded way 500 around it. The threaded way 500 is configured along a body 502 of the first electrode 120 as shown in FIG. 5. The first electrode 120 is formed by wounding a wire 504 passing through the threaded way 500 and connecting two end portions i.e. an end portion 506 and an end portion 508. The wire 504 is made of platinum. However it may be envisioned that other materials can be used to make the wire 504. The wire 504 may have its one end connected to a groove 510 present at the end portion 506. The other end of the wire 504 is wounded around groove(s) 512 and finally wounded around a fastening unit 514. In an embodiment the fastening unit 514 includes a plug unit 516 inserted into the plug in the transfer compartment 104 with a nut 518 placed on the top of the plug unit 516 for placing the first electrode 120 in the transfer compartment 104. The nut 518 may be a doom nut.

This arrangement of the fastening unit 514 enables the first electrode 120 to be conveniently placed or plugged into the transfer compartment 104. One end of the wire 304 may be wound around the plug unit 516. Further it may be appreciated that the arrangement and structure of the first electrode 120 as shown in FIG. 5 and FIG. 7 are according to an embodiment and so other embodiments may have the electrodes (i.e. the first electrode and the second electrode) with a different structure and arrangement. The second electrode 122 may have a same structural configuration of the first electrode 120 as described herein, however this structural configuration is according to an exemplary embodiment and hence other structural configurations are possible within the scope of this disclosure. The first electrode 120 and the second electrode 122 are placed within the slots 136 and 138 (as shown in FIG. 2) in the transfer compartment 104.

Figure 8:
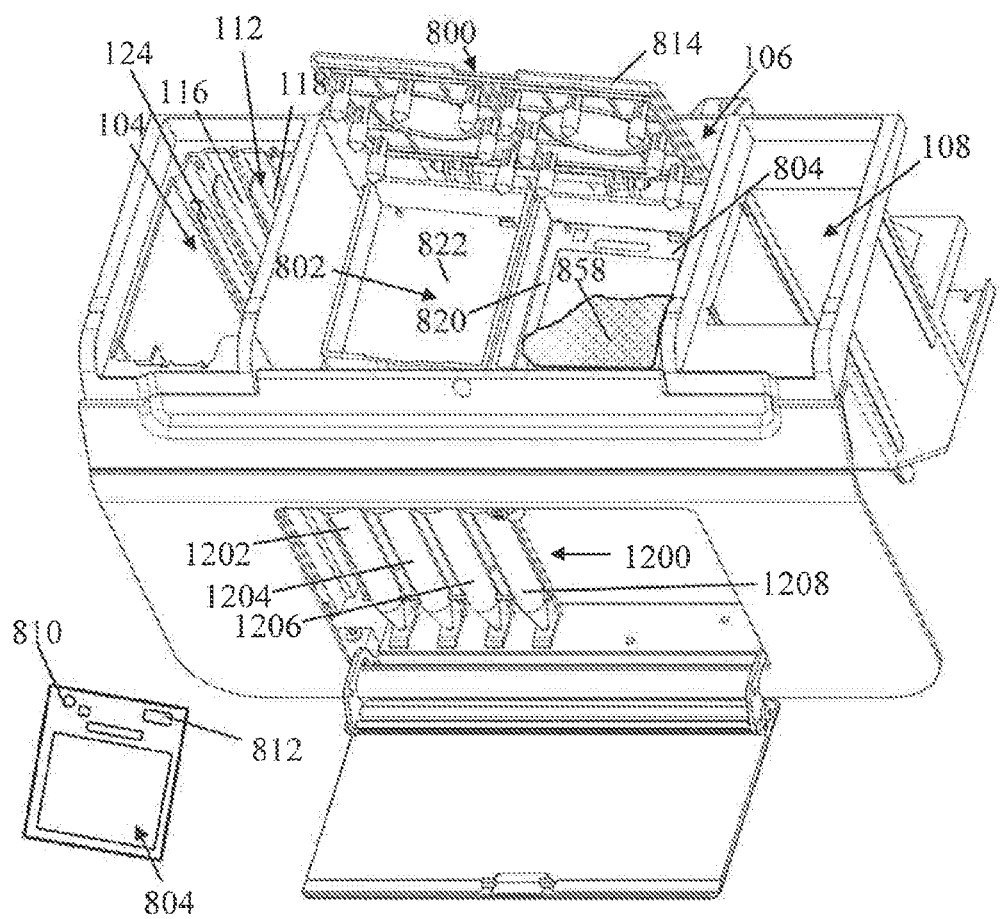
FIG. 8 is a schematic illustration of a perspective view of an agitation unit in a probing unit of the integrated system in accordance with an embodiment.

Once the proteins are transferred to the membrane from the gel member, the membrane is placed into the probing compartment 106. In the probing compartment 106, the membrane is probed using multiple antibodies and washed using other washing fluids. FIG. 8 illustrates a perspective view of the probing compartment 106 shown in the integrated system 100 in accordance with an embodiment. The probing compartment 106 includes an agitation unit 800 for holding the membrane for probing. The agitation unit 800 includes an agitation platform 802 with one or more probing chambers that can hold a membrane 804. The membrane 804 is placed in the agitation platform 802 and multiple antibodies are supplied into the agitation platform 802. In embodiment the agitation platform 802 may have elongated pins 806 and 808 that may be inserted into slots 810 and 812 respectively of the membrane 804. These slots and elongated pins help the membrane 804 to be placed in position. The geometrical structure of these elongated pins 806 and 808 may match to pass through the slots 810 and 812. For instance the elongated pin 806 may be cylindrical in structure and hence may pass through the slot 810 i.e. circular in structure. According to the disclosed embodiment, the slots 810 and 812 are compatible with or essentially identical with the elongated pins 806 and 808 of the agitation platform 802. Thus the slots of the membrane 804 may be asymmetrical in a way that it can only be fitted into a complementary pin members of an agitation platform or the like in one single way, whereby, it cannot be inserted in the wrong way, upside down or the like. Further it may be appreciated that the structure of the elongated pins of the agitation platform may vary and accordingly tile structure of the slots in the membrane also varies to be complementary with the elongated pins.

Figure 9:
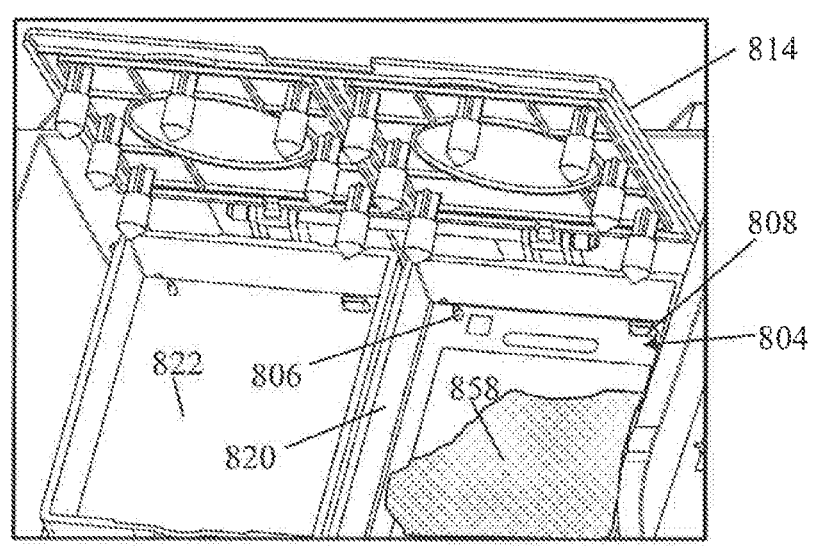
FIG. 9 is a schematic illustration of a zoomed internal view of the agitation unit in accordance with an embodiment.

The agitation unit 800 includes an opening lid 814 for opening and closing it. The opening lid 814 includes multiple protruding members such as a protruding member 816 and a protruding member 818 that facilitates the membrane 804 to be in a defined position even when the membrane 804 is agitated as shown in FIG. 9. Thus these protruding members may be in contact with the membrane 804 to restrict its movements during agitation operation.

Figure 10:
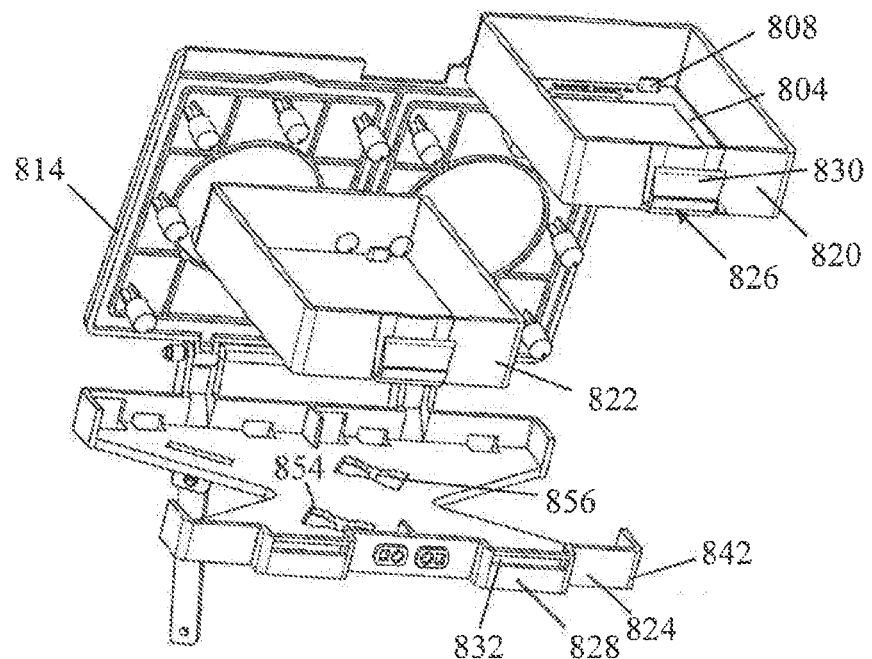
FIG. 10 is a schematic illustration of an exploded view of the agitation unit in accordance with an embodiment.

The agitation unit 800 may include two probing chambers such as a probing chamber 820 and a probing chamber 822 for placing two membranes. The membranes can be placed in these probing chambers and agitated. The probing chamber 820 holds the membrane 804. The agitation unit 800 is shown to include only two probing chambers however other agitation units including one probing chamber and more than two probing chambers may be present in the integrated system 100 according other embodiments. The agitation platform 802 includes the two probing chambers and a base 824. The two probing chambers are positioned on the base 824. The probing chambers may be fixed to the base 824 using different fastening techniques such as but not limited to screws, clasping members, clipping members, latching members and so on in different combinations of these fastening techniques. The lid 814 is provided to open and close the two probing chambers according to an embodiment. In another embodiment each probing chamber may be arranged to have a separate lid for opening and closing the probing chamber. In an embodiment a snapping member 826 of the probing chamber 820 may be fastened to a snap receiver 828 in the base 824. The snapping member 826 have a portion 830 that passes through a slot 832 in the snap receiver 828 for mounting the probing chamber 820 on the base 824. The snapping member 826 and the snap receiver 828 secure the probing chamber 820 in position on the base 824. Further the base 824 have a structure as illustrated in FIG. 10 that enables convenient arrangement of the probing chambers 820 and 822 side by side. Nevertheless it may be noted that the structure of the base of the agitation platform may vary and capable of having multiple probing chambers to hold the membranes.

Figure 11:
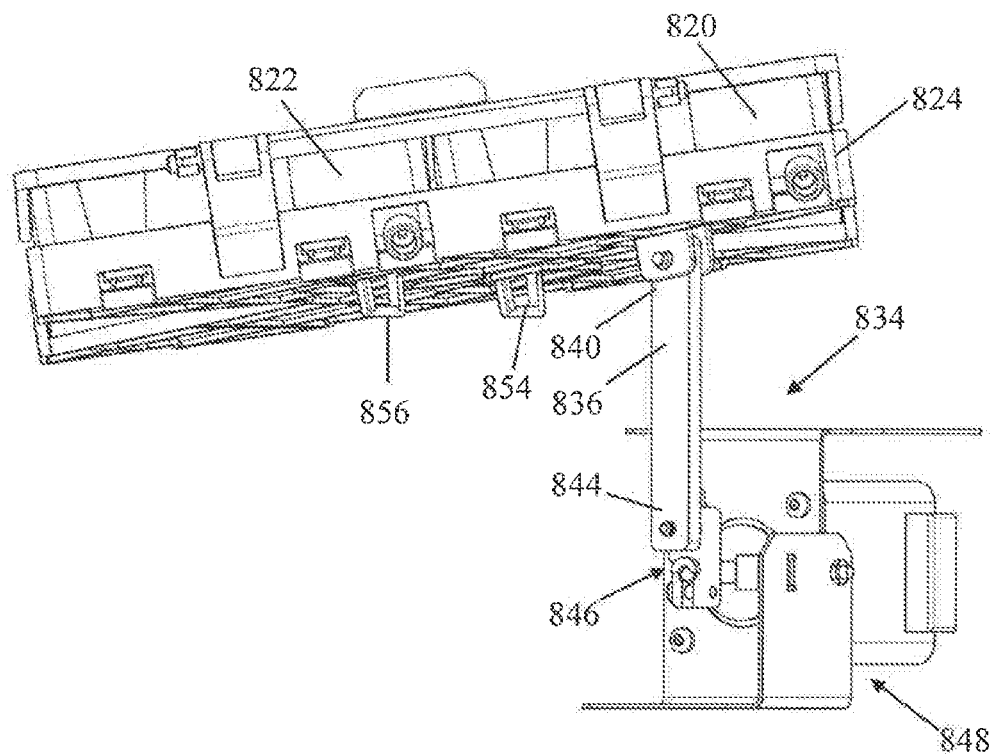
FIG. 11 is a schematic illustration of a side view of the agitation unit connected to a platform maneuvering assembly in accordance with an embodiment.

The agitation platform 802 needs to be agitated to facilitate interaction between the antibodies and the membrane 804. A platform maneuvering assembly 834 is operatively connected to the agitation platform 802 to perform these movements as schematically illustrated in FIG. 11 in accordance to an embodiment. The agitation platform 802 is pivotally mounted on a base unit 836. The base unit 836 is part of the modules holder 102. The platform maneuvering assembly 834 includes a connecting rod 838 that passes through a slot 836-1 in the base unit 836 to connect to a bottom portion of the agitation platform 802. The connecting rod 838 have an end 840 connected to the bottom portion. In an embodiment if the agitation platform 802 is substantially rectangular in shape, the connecting rod 838 may be connected to a position diagonal to a corner 842 of the agitation platform 802. The connecting rod 838 have an end 844 connected to a crank 846. The crank 846 is connected to a motor assembly 848. During operation the motor assembly 848 functions to rotate the crank 846. The rotational motion of the crank 846 results in linear motion of the connecting rod 838. The connecting rod 838 movements enable the agitation platform 802 to move in a diagonal orientation. Further as the agitation platform 802 is pivotally mounted on the base unit 836, a see-saw motion in a diagonal direction can also be achieved resulting in effective interaction of the antibodies with the membrane 804. The volume of the primary antibody may be extremely low and then needs this agitation for even spreading of the antibody and effective interaction with proteins on the membrane. In an embodiment the agitation platform 802 may be moved to achieve 3-dimensional movements thereby ensuring effective spreading of the antibodies with the membrane 804. This is because the antibodies in the liquid form may move vigorously in the agitation platform 802 to probe the membrane 804. The agitation platform 802 is pivotally connected at a protruding member 850 and a protruding member 852 configured on the base unit 836. Pivot units 854 and 856 at the bottom of the agitation platform 802 are configured on the protruding member 850 and the protruding member 852 respectively. The pivot units 854 and 856 may be connected or arranged on the protruding member 850 and the protruding member 852 using different arrangements in accordance with other embodiments which are not shown in FIG. 11. Thus the agitation platform 802 moves in a see-saw fashion with respect to the protruding member 850 and the protruding member 852. In an embodiment the protruding member 850 and the protruding member 852 are positioned diagonally with respect to each other rendering the see-saw movements possible. It may be appreciated that in other embodiments the protruding members may be arranged in different positions and operating mechanisms other than the pivot units 854 and 856 may be used for implementing the movements of the agitation platform 802.

The movement of the agitation platform 802 may be controlled by a control unit (not shown in FIGS. 8-11). The control unit controls the operation of the motor assembly 848 and thereby automatically controls the rotational motion of the crank 846 and in turn the linear motion of the connecting rod 838. Thus the control unit regulates the amount of agitation movements based on the requirement i.e. amount of agitation movements required to facilitate complete interaction between the antibodies and the membrane 804.

When an antibody 858 interacts with the membrane 804 as shown in FIG. 9 the antibody 858 binds with proteins of interest present in the membrane 804. The left over antibody 858 may be drained out from the agitation platform 802 using pumping and draining system provided in the probing compartment 106. The pumping and the draining system are connected to the agitation platform 802 to supply the antibody 858 and drain the leftover antibody 858. Then the pumping system may supply water into the agitation platform 802 to wash the probed membrane 804. Thereafter the membrane 804 may be again probed using another antibody. Here it may be also appreciated that the order of washing, blocking and probing the membrane 804 using the water and antibodies may be performed in different orders without deviating from the scope of the disclosure. Thus the membrane 804 may be washed by water only when the membrane 804 is probed with all antibodies that can bind with the proteins. Different antibodies may bind with different proteins of interest during the probing process.

Further a side wall 860 of the probing compartment 106 may have cut outs 862 and 864 so that tubes and the pumping and draining systems can be connected to the agitation platform 802. The tubes include supply tubes for supplying the antibodies into the agitation platform 802 and draining tubes for draining the leftover antibodies. There may be also tubes that supply washing fluids such as water to the agitation platform 802.

Figure 12:
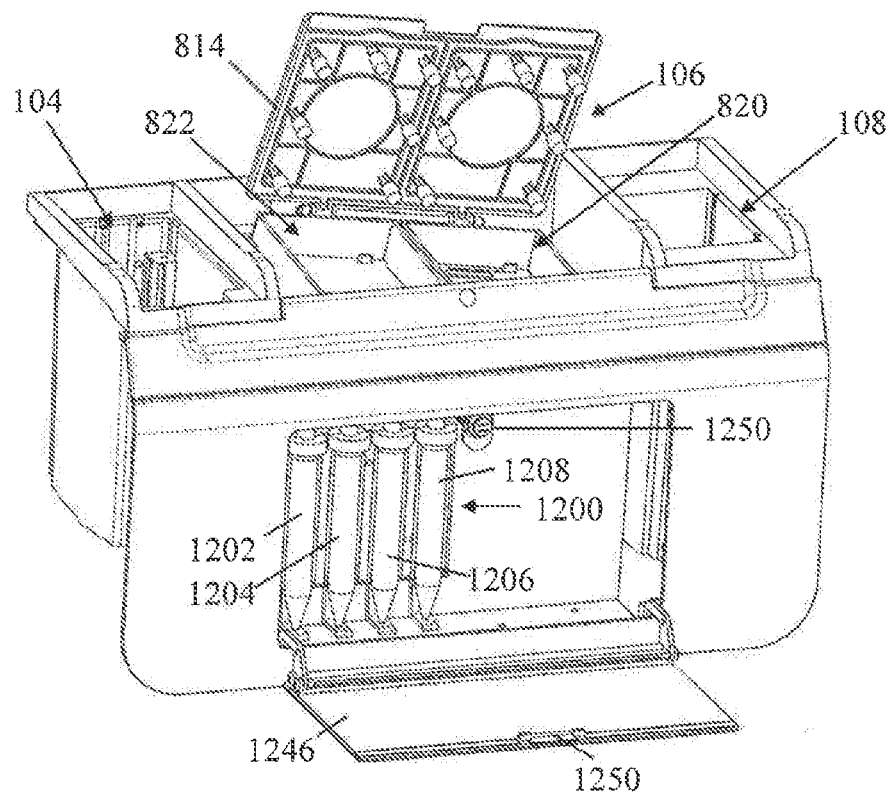
FIG. 12 is a schematic illustration of the integrated system including the agitation unit and supply unit in accordance with another embodiment.

The antibodies may be supplied from a supply unit 1200 arranged in the modules holder 102 of the integrated system 100 as shown in FIG. 12 in accordance with an embodiment. The supply unit 1200 includes multiple tubes storing different antibodies. As illustrated four tubes such as a tube 1202, a tube 1204, a tube 1206 and a tube 1208 are part of the supply unit 1200 for supplying the antibodies. The antibodies include a primary antibody and a secondary antibody. During the probing (detection) process the primary antibody is directed towards the protein of interest and secondary antibody e.g. for the protein of interest with a modified antibody which is linked to a reporter enzyme; when exposed to an appropriate substrate this enzyme drives a colorimetric reaction and produces a colour or by fluorescently labelled targets (dyes), that may be detected by a suitable imaging technique. The primary antibody may be stored in the tubes 1202 and 1206; and the secondary antibody may be stored in the tubes 1204 and 1208. The tubes 1202-1208 may be Falcon™ tubes according to an embodiment. In an embodiment the tubes 1202-1208 may have a cylindrical configuration with conical end.

Figure 13:
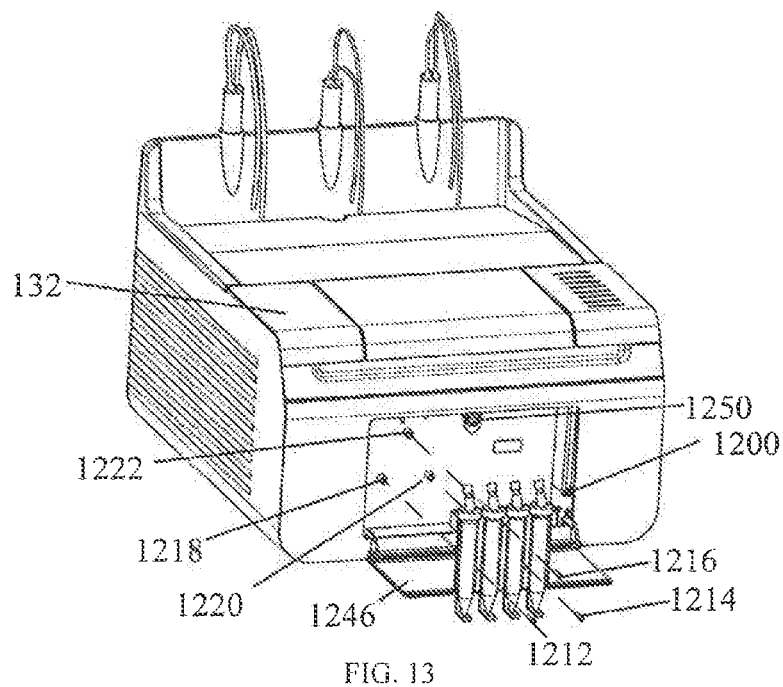
FIG. 13 is a schematic illustration of the integrated system showing the supply unit in a disconnected configuration from the probing compartment in accordance with an embodiment.

The supply unit 1200 may also include pumping system (not shown in FIG. 12) connected to the tubes 1202-1208. The pumping system operates to take the antibodies and supply to the agitation platform 802. FIG. 13 schematically illustrates the tubes 1202-1208 in a disconnected configuration from the probing compartment 106. The tubes 1202-1208 are assembled on a side wall 1210 of the modules holder 102 using multiple fastening members such as fastening members 1212, 1214 and 1216. The fastening members 1212, 1214 and 1216 are inserted onto fastener receivers 1218, 1220 and 1222 respectively. In an embodiment the fastening members 1212, 1214 and 1216 may include screw members. It may be also envisioned that the tubes 1202-1208 may be arranged in the probing compartment 106 using other fastening units such as velcro belt units, snapping members, pins and so on.

Figure 14:
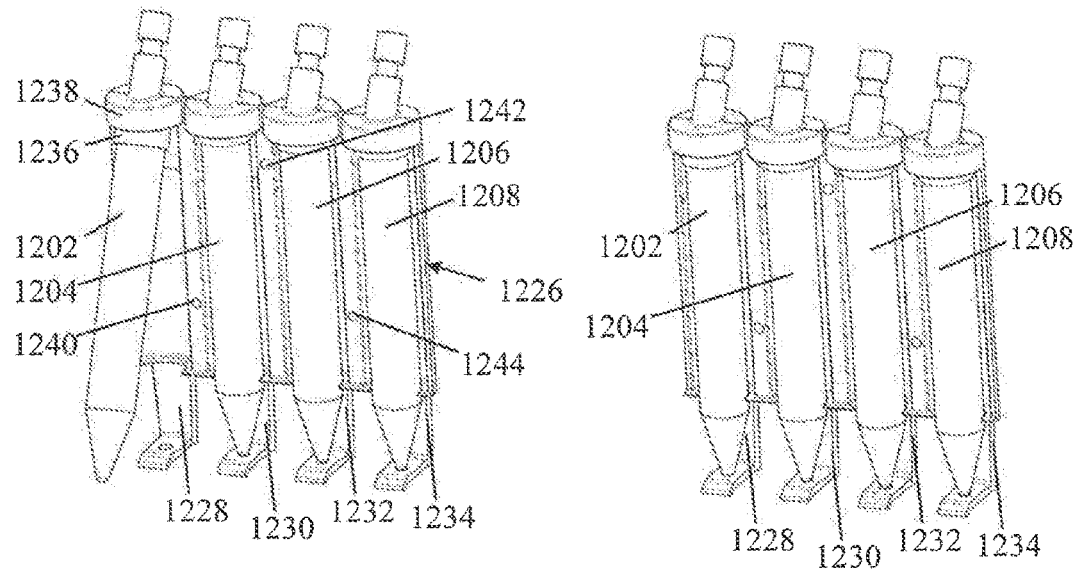
FIGS. 14 and 15 illustrate perspective and front view of the supply unit in accordance with an embodiment.
Figure 15:
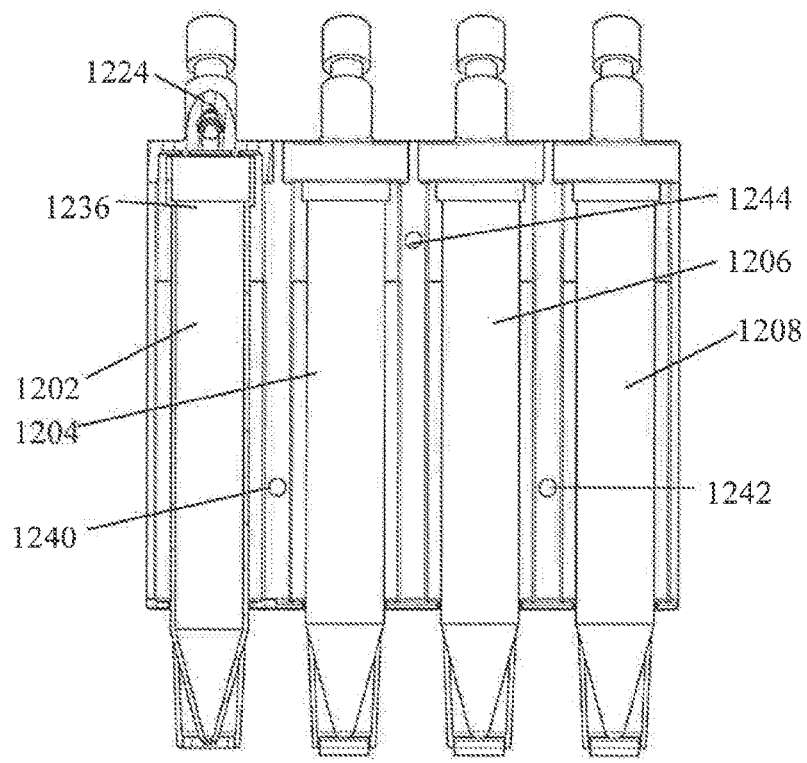

The tubes 1202-1208 may be connected to the pumping system through respective delivery tubes. For example the tube 1202 is connected to a delivery tube 1224. The tubes 1202-1208 are arranged on to a supporting unit 1226 having multiple slits. The tubes 1202-1208 are arranged into racks 1228, 1230, 1232 and 1234 respectively. The tube 1202 may be inserted into the slit 1228 may be by snap fitting an end 1236 of the tube 1202 to a receiver 1238. The receiver 1238 may have a circular configuration according to an embodiment. The end 1236 of the tube 1202 gets inserted into the received 1238 when the user inserts the tube 1202 at an angle as illustrated in FIG. 14 according to an embodiment. FIG. 14 schematically illustrates different loading and loaded configurations of the tubes 1202-1208. In the loading configuration, the tube 1202 is aligned at an angular position to be inserted into the receiver 1238. Whereas in the loaded configuration all the tubes 1202-1208 are arranged in their respective racks 1228, 1230, 1232 and 1234. The supporting unit 1226 holding the tubes 1202-1208 are fastened to the side wall 1210 by passing the fastening members 1212, 1214 and 1216 through holes 1240, 1242 and 1244 respectively to connect to the fastener receivers 1218, 1220 and 1222. The supply unit 1200 and its configuration as illustrated in FIGS. 12, 13 and 14 are according to an embodiment, however the supply unit 1200 may have different configuration for supplying the antibodies into the agitation platform 802.

The integrated system 100 includes an opening member 1246 for closing a portion of the probing compartment 106 as shown in FIG. 13. The opening member 1246 may be pivotally connected to a body 1248 of the integrated system 100. The opening member 1246 is opened and closed to access the tubes 1202-1208. In other embodiments the opening member 1246 may have different configurations and arranged in the integrated system 100. The opening member 1246 includes a locking unit 1250 for closing the portion of the probing compartment 106. The locking unit 1250 as shown in FIG. 12 may be a magnetic unit. In other embodiments the locking units used may have a different configuration and arrangement.

Figure 16:
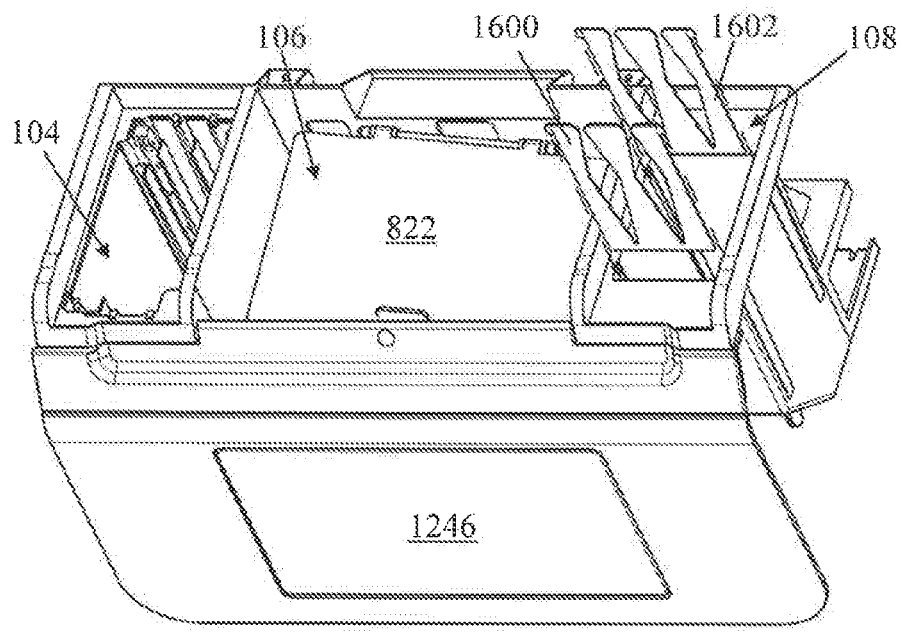
FIG. 16 illustrate a perspective view of membrane holders in a dryer unit of the modules holder in accordance with an embodiment.

Once probing of the membrane 804 using the antibodies is completed it is washed using the washing fluid i.e. water. As the membrane 804 is wet it needs to be dried in the dryer compartment 108. FIG. 16 illustrates an exploded view of the dryer compartment 108 holding membrane holders in accordance with an embodiment. The dryer compartment 108 is shown to include two membrane holders 1600 and 1602. The membrane holders 1600 and 1602 may be inserted and positioned within the dryer compartment 108. Multiple lots (not shown in FIG. 16) are provided within the dryer compartment 108 where the membrane holders 1600 and 1602 are slid and assembled. In another embodiment the membrane holders 1600 and 1602 may be an integral part of the dryer compartment 108. In this case the dryer compartment 108 may be a single molded unit including the membrane holders 1600 and 1602. In yet another embodiment the membrane holders 1600 and 1602 may be fastened within the dryer compartment 108.

The membrane holders 1600 and 1602 may be made of sheet metal. In another embodiment the membrane holders 1600 and 1602 may be made of a plastic material. However in other embodiment the membrane holders 1600 and 1602 may be made of any other materials that make them flexible for usage.

Figure 17:
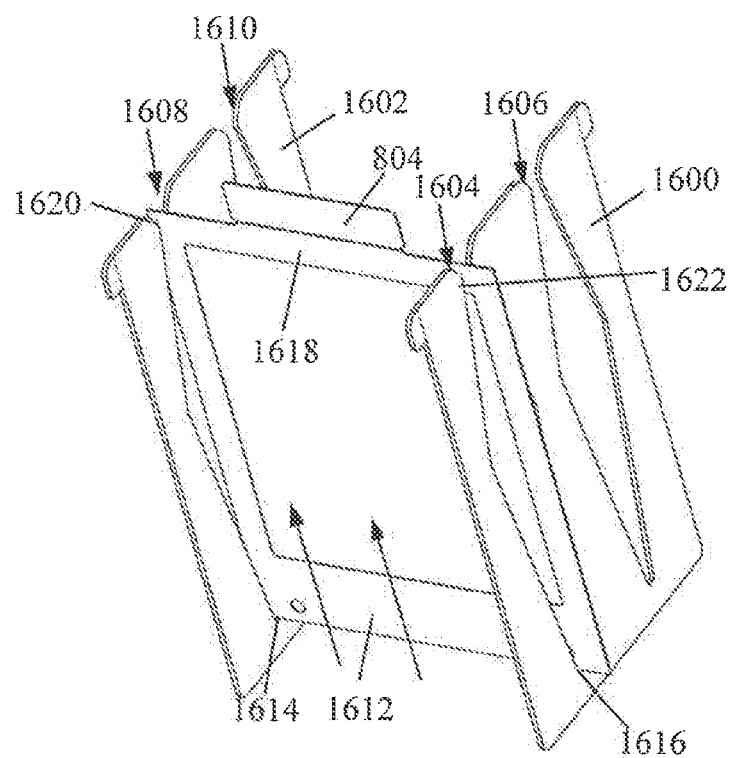
FIGS. 17 and 18 is a schematic illustration of a perspective view and a front view of the membrane holders in accordance with an embodiment.

These membrane holders may include slits for holding the membrane. Now considering the membrane holder 1600, this includes two slits such as a slit 1604 and a slit 1606. The slits 1604 and 1606 have a shape such that only minimum contact exists with the membrane 804 when positioned in the membrane holder 1600. For instance the slit 1604 may have a diamond shape. As shown in FIG. 17, the membrane 804 is positioned in the slits of the membrane holders 1600 and 1602. The membrane holder 1602 includes a slit 1608 and a slit 1610. The membrane holder 1600 and the membrane holder 1602 are positioned side by side so that the slit 1604 is aligned in line with the slit 1608. Thus two membrane holders are required for holding the membrane 804. Similarly the slit 1606 is aligned with the slit 1610. As illustrated in FIG. 17, when the membrane 804 is placed in the membrane holders 1600 and 1602, end portions of the membrane 804 will be in contact with ends of the slits 1608 and 1610. More specifically an end portion 1612 of the membrane 804 touches an end 1614 of the slit 1608 and an end 1616 of the slit 1604. Further an end portion 1618 of the membrane 804 touches an end 1620 of the slit 1608 and an end 1622 of the slit 1604. Points in the slit 1608 where the membrane 804 are in contact may be points 1624 and 1626. Thus only minimum contact exists between the membrane holders 1600 and 1602 and the membrane 804. As a result any damage caused due to placing the membrane 804 in the membrane holder 1600 is avoided. Moreover efficient drying of the membrane 804 can also be achieved.

The dryer compartment 108 also includes an air supply unit such as a fan or any other drying unit configured to blow air along the membrane 108 to dry them. The air may blow along the surface of the membrane 108 indicated by the arrows 1628 and 1630. The air blown may be hot air that dries the membrane 108. As the contact between the membrane 804 and the membrane holder 1600 is very minimum when the hot air passes proximal to the surface of the membrane 108 its dries the membrane 108 effectively. This is achieved because a major portion of the surface of the membrane 108 is exposed to the hot air. While drying the membrane 108 a lid of the drying compartment 108 may be closed. The lid includes multiple openings for allowing the hot air flowing through the membrane 108 to flow out. So the water present in the membrane 108 is evaporated by the hot air and flow out carrying the vapors thereby drying the membrane 108. The lid may have different configurations other than as described with respect to FIG. 1 which allows the hot air to dry the membrane 108 and flow out.

Figure 18:
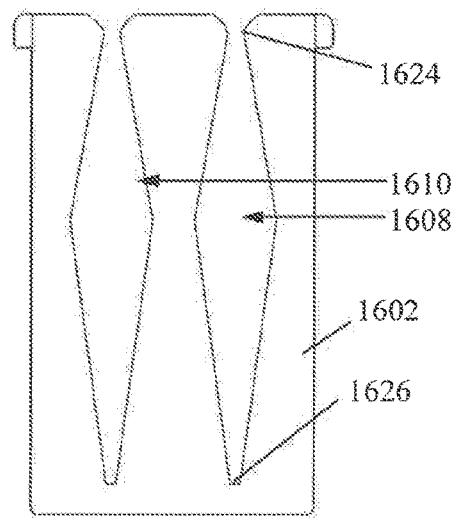

The membrane holders can also have more slits than two slits provided (as illustrated in FIG. 17 and FIG. 18) so that more than two membranes can be held in the membrane holders.

Figure 19:
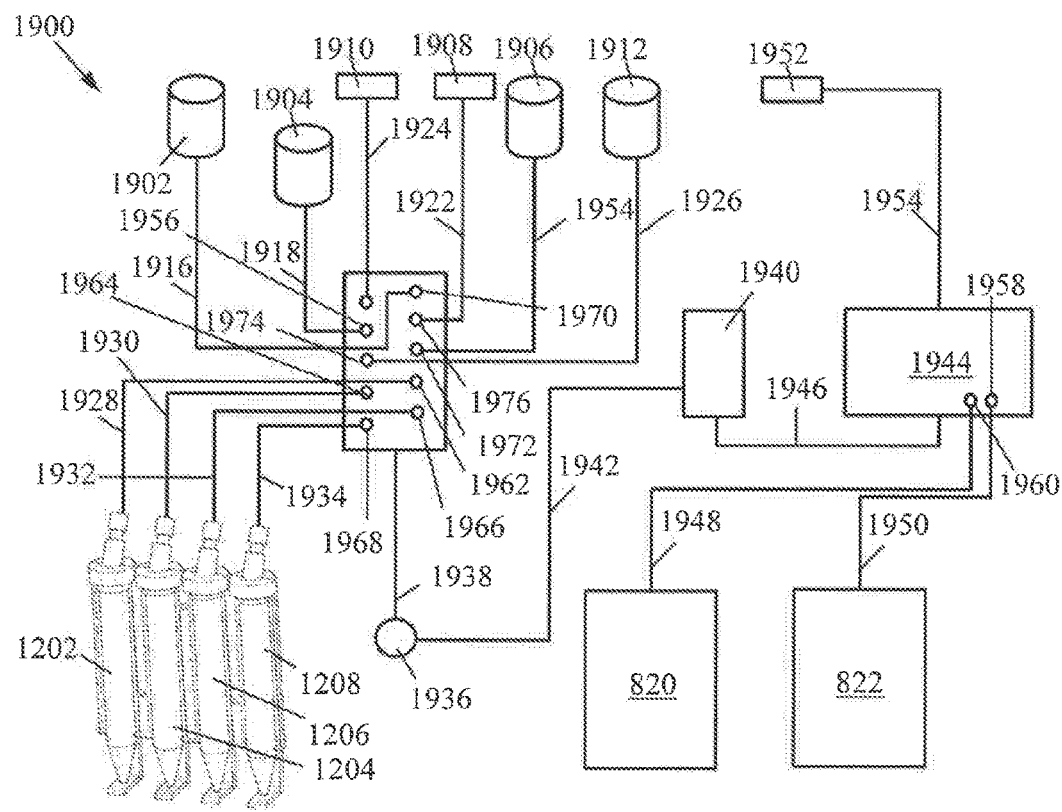
FIG. 19 is a schematic illustration of multiple storage units connected a fluid pumping system 1900 for a probing compartment 106 in accordance with an embodiment.

Turning now to FIG. 19 schematically illustrating multiple storage units connected a fluid pumping system 1900 for a probing compartment 106 in accordance with an embodiment. The multiple storage units include a storage unit 1902 storing water, a storage unit 1904 storing a blocking solution, a storage unit 1906 storing a first washing fluid, a storage unit 1908 storing a custom solution such as NaOH, a storage unit 1910 storing waste fluid and a storage unit 1912 for storing a second washing fluid. Multiple supply tubes are also present to connect these storage units to a probing valve controller 1914 which is part attic fluid pumping system 1900. For example a tube 1916 connects the storage unit 1902 to the probing valve controller 1914, a tube 1918 connects the storage unit 1904 to the probing valve controller 1914, a tube 1920 connects the storage unit 1906 to the probing valve controller 1914, a tube 1922 connects the storage unit 1908 to the probing valve controller 1914, a tube 1924 connects the storage unit 1910 to the probing valve controller 1914, and a tube 1926 connects the storage unit 1912 to the probing valve controller 1914.

Further illustrated in FIG. 19 are the tubes 1202-1208 holding the antibodies connected to the probing valve controller 1914. The tubes 1202, 1204, 1206 and 1208 are connected to the probing valve controller 1914 using a tube 1928, a tube 1930, a tube 1932 and a tube 1934. The probing valve controller 1914 is also connected to a pump 1936 using a tube 1938. The probing valve controller 1914 decides to select a solution i.e. a washing fluid, water, a blocking fluid, a transfer buffer and so on to be pumped. The pump 1936 is connected to a sensor 1940 using a tube 1942. The sensor 1940 is connected to a selector valve 1944 using a tube 1946. The sensor 1940 is used to detect if air is trapped in the tube 1942 and the tube 1946. The selector valve 1944 is connected to the probing chamber 820 and the probing chamber 822 of the agitation unit 800 using a tube 1948 and a tube 1950 respectively. The selector valve 1944 is also connected to a waste outlet 1952 using a tube 1954.

During a probing process, initially the probing chambers 820 and 822 are filled with the blocking solution stored in storage unit 1904. The blocking solution passes through a valve 1956 opened by the probing valve controller 1914 and then passes through the pump 1936, the sensor 1040 and the selector valve 1944 to reach the probing chambers 822 and 820. The selector valve 1944 opens a valve 1958 and a valve 1960 to supply the blocking solution to the probing chambers 822 and 820 respectively. Once the membrane 804 are placed in a probing chamber such as the probing chambers 820 and 822, the membrane 804 are washed using washing fluids (i.e. the first washing fluid and the second washing fluid), blocking solution, a primary antibody and a secondary antibody. The blocking solution is used to block proteins that are not of interest present in the membrane 804. This ensures that the blocked proteins are not probed by the antibodies. The membrane 804 may be blocked using the blocking solution that may be pre-filled in the probing chambers 820 and 822.

The primary antibody and the secondary antibody are stored in the tubes 1202-1208. The tubes 1202, 1204, 1206 and 1208 are connected to valves 1962, 1964, 1966 and 1968 respectively using the tubes 1928, 1930, 1932 and 1934. Based on the antibody to be supplied from the tubes 1202-1208 the probing valve controller 1914 opens an appropriate valve from the valves 1962, 1964, 1966 and 1968. The selected antibody then passes through the pump 1936, the sensor 1040 and the selector valve 1944 to reach the probing chambers 822 and 820. The selector valve 1944 opens the valve 1958 and the valve 1960 to supply the selected antibody to the probing chambers 822 and 820 respectively. Once the membrane 804 is washed using the antibodies and the washing fluid, a waste solution left over is pumped out the waste outlet 1952 through the selector valve 1944. If the waste solution is collected from the probing chamber 822 then the valve 1958 is opened to send the waste solution to the waste outlet 1952. Further if the waste solution is collected from the probing chamber 820 then the valve 1960 is opened to send the waste solution to the waste outlet 1952.

Water stored in the storage unit 1902 is supplied to the probing chamber 820 or 822 by first passing through a valve 1970 opened by the probing valve controller 1914. The water passes through the pump 1936, the sensor 1040 and the selector valve 1944 to reach the probing chambers 822 or 820. The selector valve 1944 opens the valve 1958 or the valve 1960 to supply water to the probing chambers 822 or 820 respectively. Further the first washing fluid is supplied to the probing chamber 820 or 822 by first passing through a valve 1972 opened by the probing valve controller 1914. The first washing fluid passes through the pump 1936, the sensor 1040 and the selector valve 1944 to reach the probing chambers 822 or 820. The selector valve 1944 opens the valve 1958 or the valve 1960 to supply the selected first washing fluid to the probing chambers 822 or 820 respectively. The second washing fluid is supplied to the probing chamber 820 or 822 by first passing through a valve 1974 opened by the probing valve controller 1914. The second washing fluid passes through the pump 1936, the sensor 1040 and the selector valve 1944 to reach the probing chambers 822 or 820. The selector valve 1944 opens the valve 1958 or the valve 1960 to supply the second washing fluid to the probing chambers 822 or 820 respectively.

Further the custom solution such as NaOH is supplied to the probing chamber 820 or 822 by first passing through a valve 1976 opened by the probing valve controller 1914. The custom solution passes through the pump 1936, the sensor 1040 and the selector valve 1944 to reach the probing chambers 822 or 820. The selector valve 1944 opens the valve 1958 or the valve 1960 to supply the custom solution to the probing chambers 822 or 820 respectively.

Figure 20:
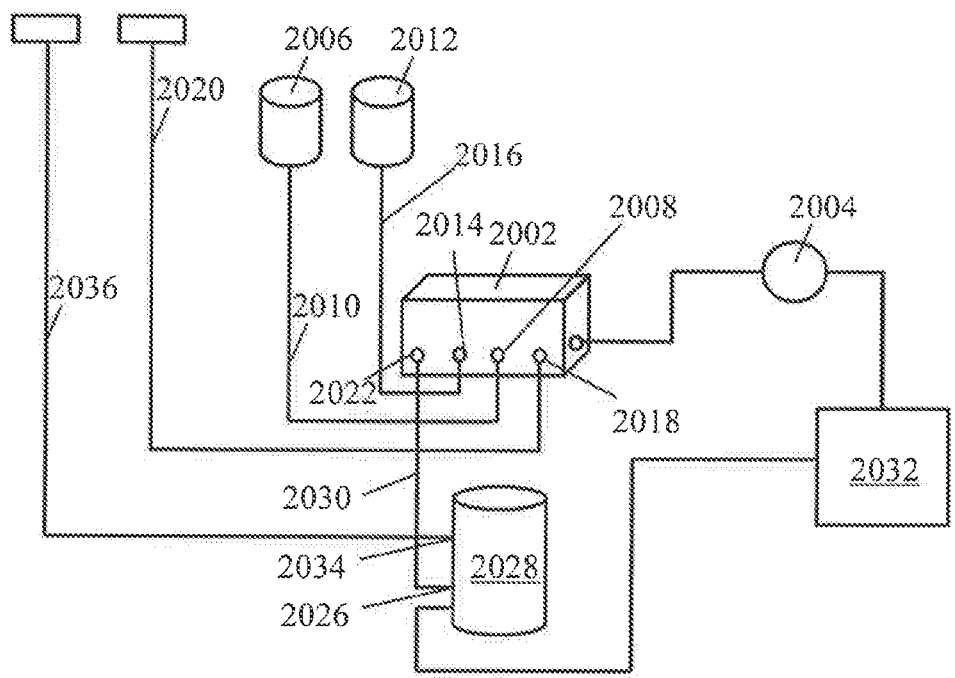
FIG. 20 is a schematic illustration of a pumping system connected to storage units for a transfer compartment in accordance to an embodiment.

Now referring to FIG. 20 schematically illustrating a pumping system 2000 connected to storage units for a transfer compartment 104 in accordance to an embodiment. The pumping system 2000 includes multiple tubes connected to the storage units, a transfer valve controller 2002 and a pump 2004. A storage unit 2006 storing water is connected to a valve 2008 of the transfer valve controller 2002 using a tube 2010. Another storage unit 2012 storing a transfer buffer is connected to a valve 2014 of the transfer valve controller 2002 using a tube 2016. A valve 2018 of the transfer valve controller 2002 is connected to a waste outlet 2020. Further a valve 2022 of the transfer valve controller 2002 is connected to an inlet 2026 of a transfer tank 2028 using a tube 2030.

To initiate an electrophoretic process (i.e. the transfer process muster tank 2028 is filled with the transfer buffer stored in the storage unit 2012. During the transfer process, the transfer buffer is pumped using the pump 2004 so as to pass the transfer buffer through the transfer tank 2028, a cooling unit 2032 and the transfer valve controller 2002. The cooling unit 2032 is capable of cooling the transfer buffer to maintain it at a room temperature. If the transfer buffer stored in the transfer tank 2028 overflows beyond a predefined level then the transfer buffer passes out through an overflow outlet 2034 and pass through a tube 2036. Further any waste solution present in the transfer tank 2028 is pumped using the pump 2004 through the transfer valve controller 2002, the valve 2018 to the waste outlet 2020. Once the electrophoretic process is complete the pump 2004 is used to pump the water from the storage unit 2006 to pass through the transfer valve controller 2002 using the valve 2008. The water is supplied into the transfer tank 2028 and the fluid path to the transfer tank 2028 to clean it. The water may be ultra pure water. The waste fluid after cleaning is pumped out of the fluid path and the transfer tank 2028 through the waste outlet 2020. The fluid path refers to the tube 2016 connecting the valve 2014 of the transfer valve controller 2002 and the storage unit 2012 and the tube 2030 connecting the transfer valve controller 2002 and the inlet 2026.

Figure 21:
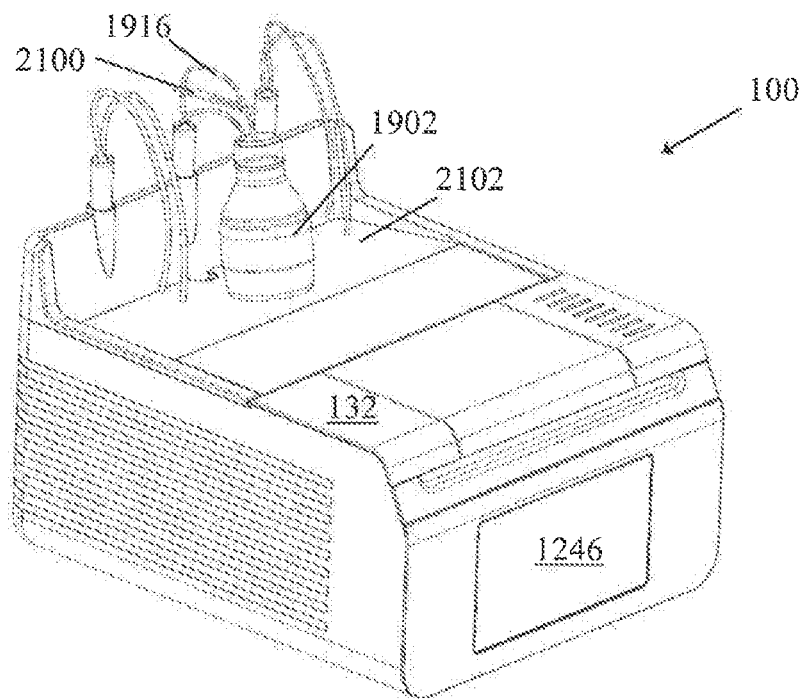
FIGS. 21 and 22 illustrate a tubing holder for holding a tube in the integrated system in accordance with an embodiment.
Figure 22:
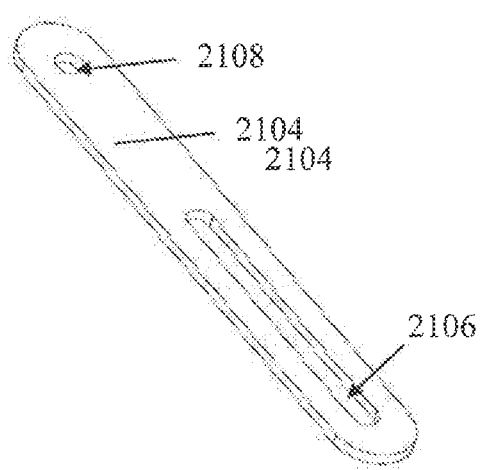

FIGS. 21 and 22 illustrate a tubing holder 2100 for holding multiple tubes in the integrated system 100 in accordance with an embodiment. The storage unit 1902 storing water is placed on a platform 2102 and connected to the tube 1916. The tube 1916 is held by the tubing holder 2100. The tube 1916 may be a stiff tube and hence may not remain in a defined orientation so as to keep the storage unit 1902 on the platform 2102. The tube 1916 may be made of a stiff material that does not always remain in a folded position as shown in FIG. 21. The tube 1916 may extend throwing out the storage unit 1902 from the platform 2102. The storage unit 1902 may be overthrown when water content is reduced due to usage. To keep the tube 1916 in the defined orientation a tube holder 2104 is clamped to the tube 1916. The tube holder 2104 includes a slit way 2106 through which the tube 1916 passes to hold the tube 1916 in position thereby preventing over throwing of the storage unit 1902. More specifically the tube 1916 passes through a hole 2108 and thereafter through the slit way 2106 for remaining in the defined orientation. The tube holder 2104 prevents the tube 1916 from extending. The tube holder 2104 is made of but not limited to a plastic material and sheet metal.

Figure 23:
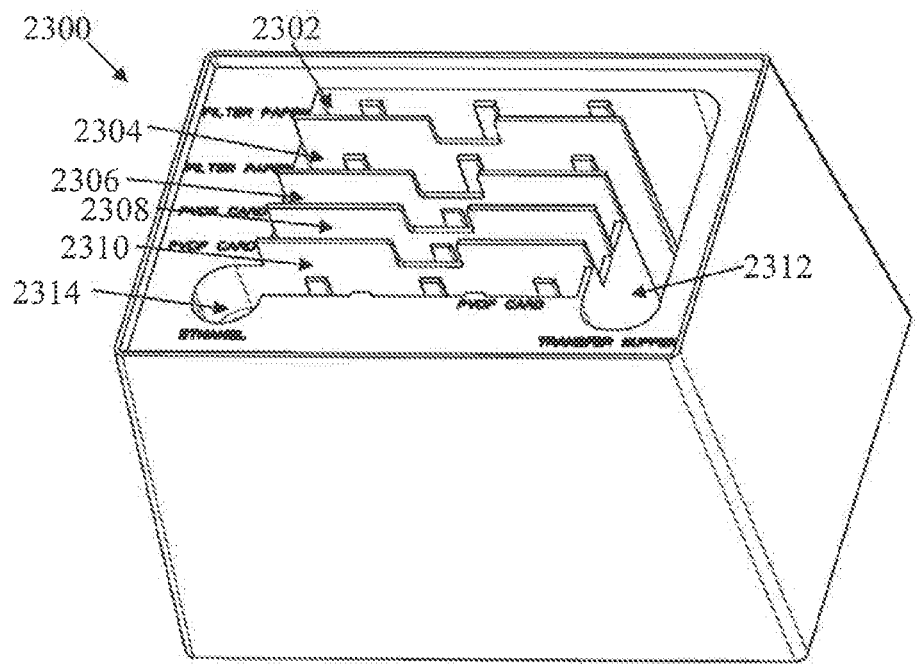
FIGS. 23 and 24 illustrate a perspective and top view of a card holder used during the electro-blotting, a blotting and drying process in accordance with an embodiment.
Figure 24:
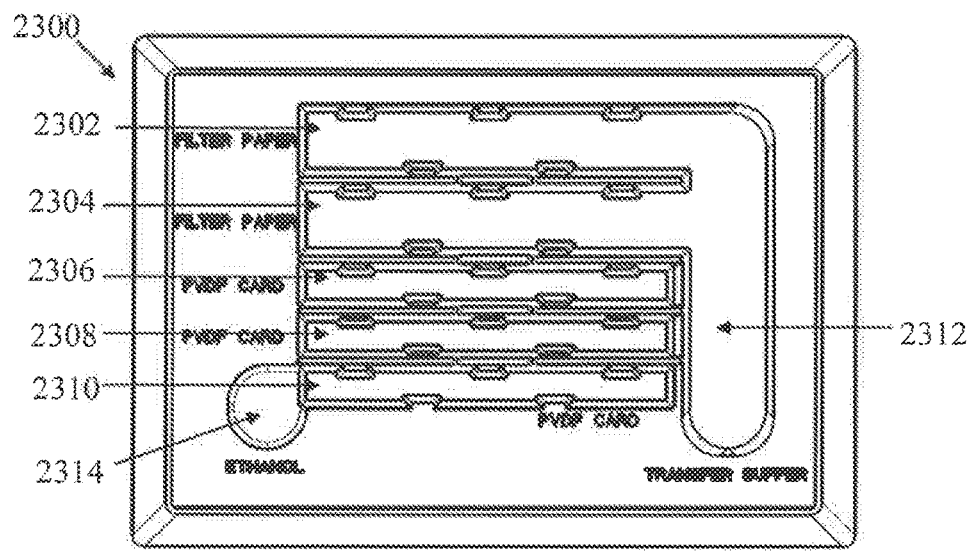

FIGS. 23 and 24 illustrate a perspective and top view of a card holder 2300 used during the electrophoretic process, a blotting and drying process in accordance with an embodiment. The card holder 2300 includes multiple holder slots such as a holder slot 2302, a holder slot 2304, a holder slot 2306, a holder slot 2308 and a holder slot 2310. The holder slot 2302 and the holder slot 2304 may hold filter pads. The holder slots 2306, 2308 and 2310 may hold membranes i.e. PVDF cards (such as the membrane 804). The holder slat 2302 and the holder slot 2304 are connected to a reservoir 2312. The reservoir 2312 holds a fluid such as transfer buffer which is supplied to the holder slots 2302 and 2304. Further another reservoir 2314 holds a fluid such as ethanol which is supplied to the holder slots 2306, 2308 and 2310. When the filter pads and the membranes are placed in the holder slots they are oriented in a vertical position and immersed in the transfer buffer and ethanol. Further even though the card holder 2300 is illustrated to have five holder slots, a card holder can be arranged to include more than five holder slots or less than five holder slots and may also include more than two reservoirs or a single reservoir in accordance with other embodiments. The card holder 2300 may be used between the electrophoretic process, a blotting and drying process when moved from each compartments of the modules holder 102. Further before the electrophoretic process a transfer sandwich including filter pads, a membrane and a gel member is thrilled. Before making the transfer sandwich these filter pads, the membrane and the gel member may be placed in the holder slots of the card holder 2300 thereby enabling a user to conveniently handle them. This also avoids placing of the filter pads, the membrane and the gel member in other locations that can result in mishandling causing defects.

Figure 25:
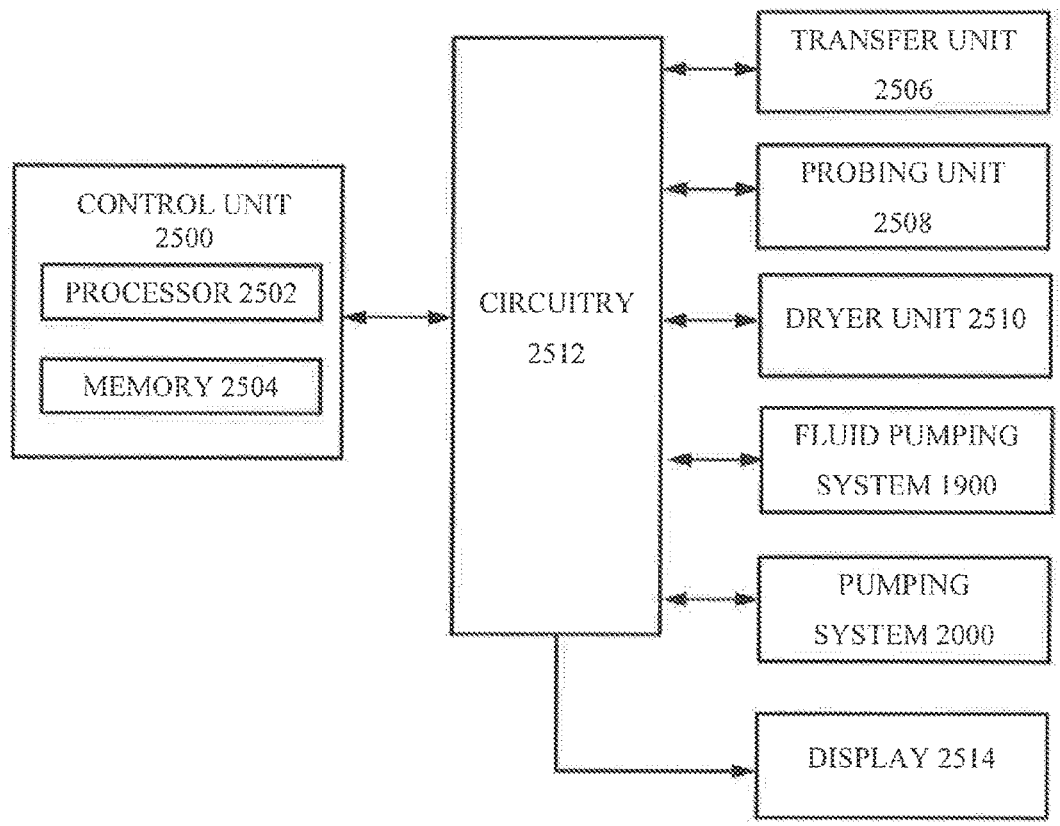
FIG. 25 is a block diagram of control unit for controlling the operations of the electro-blotting, a blotting and drying process in an integrated system in accordance with an embodiment.

FIG. 25 is a block diagram of control unit 2500 for controlling the operations of the electrophoretic process, a blotting and drying process in an integrated system 100 in accordance with an embodiment. The control unit 2400 includes a processor 2502 and a memory 2504. The processor 2502 of the illustrated example is a hardware. For example, the processor 2502 can be implemented by one or more integrated circuits, logic circuits, microprocessors or controllers or microcontrollers. The memory 2504 may be a Synchronous Dynamic Random Access Memory (SDRAM), Dynamic Random Access Memory (DRAM), RAMBUS Dynamic Random Access Memory (RDRAM) and/or any other type of random access memory device, or any hardware memory.

The processor 2502 may communicate with a transfer unit 2506, a probing unit 2508, a dryer unit 2510, the fluid pumping system 1900 and the pumping system 2000 through a circuitry 2512. The processor 2502 may be programmed and configured to operate the transfer unit 2506, the probing unit 2508 and the dryer unit 2510 based on settings input by a user. A display 2514 may be present through which the settings can be input. The display 2512 is controlled by the processor 2502 through the circuitry 2512. The display 2512 is also configured to control indicators provided in the integrated system 100 for each units i.e. the transfer unit 2506, the probing unit 2508 and the dryer unit 2510. These indicators may show the different stages such as start-up, ready, running, warning and so on associated with operation of each unit.

The circuitry 2512 may be implemented by any type of interface standard, such as an Ethernet interface, a universal serial bus (USB), and/or a PCI express interface, a transmitter, a receiver, a transceiver, a modem and/or network interface card to facilitate exchange of data with external machines (e.g., computing devices of any kind), integrated circuits, analog or digital circuit(s), logic circuits, programmable processor(s), application specific integrated circuit(s) (ASIC(s)), programmable logic device(s) (PLD(s)) and/or field programmable logic device(s) (FPLD(s)).

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor. As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The methods described herein can be performed using a processor or any other processing device. The method steps can be implemented using coded instructions e.g., computer readable instructions) stored on a tangible computer readable medium. The tangible computer readable medium may be for example a flash memory, a read-only memory (ROM), a random access memory (RAM), any other computer readable storage medium and any storage media. Although the method of projecting images onto one or more walls and a ceiling using in-built image projecting units in a medical imaging apparatus is explained with reference to the flow chart of figures, other methods of implementing the method can be employed. For example, the order of execution of each method steps may be changed, and/or some of the method steps described may be changed, eliminated, divide or combined. Further the method steps may be sequentially or simultaneously executed for controlling the operations of the electrophoretic process, a blotting and drying process in an integrated system 100.

From the foregoing, it will appreciate that the above disclosed integrated system for performing for electro-blotting and blotting provide numerous benefits to healthcare enterprises, such as improved proteins separation, single device to perform electro-blotting and blotting, and among others. Ultimately these advantages result in reduced cost and efficient handling of the membranes used for separating the proteins.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An integrated system for electro-blotting and blotting comprising:
    a transfer unit for receiving at least one transfer sandwich holder, each transfer sandwich holder holding a transfer sandwich comprising a gel member and a membrane, wherein the transfer unit is configured to transfer samples from the gel member to the membrane;
    a probing unit for receiving the membrane there within, the membrane is exposed to a plurality of antibodies for binding with the samples in the membrane; and
    a drying unit for drying the membrane with hot air.

2. The integrated system according to claim 1 further comprises a modules holder comprising a transfer compartment for holding the transfer unit, a probing compartment for holding the probing unit and a dryer compartment for holding the drying unit.

3. The integrated system according to claim 1, wherein the transfer unit comprises:
    at least one sandwich slot for holding a transfer sandwich holder of the at least one transfer sandwich holder; and
    a plurality of electrodes for facilitating the transfer of samples from the gel member to the membrane in presence of a transfer buffer.

4. The integrated system according to claim 3, wherein an electrode of the plurality of electrodes comprises:
    a fastening unit for arranging the electrode within a sandwich slot of e at least one sandwich slot; and
    at least one wire wounded around the electrode.

5. The integrated system according to claim 3, wherein the plurality of electrodes comprises a first electrode and a second electrode, the transfer sandwich holder is positioned between the first electrode and the second electrode.

6. The integrated system according to claim 3 fluffier comprises a transfer buffer supplier for supplying the transfer buffer into the transfer unit.

7. The integrated system according to claim 2, wherein the probing unit comprises:
    an agitation unit for holding the membrane and capable of performing agitation operation for interacting the plurality of antibodies with samples in the membrane; and
    a supply unit for supplying the plurality of antibodies into the agitation unit.

8. The integrated system according to claim 7, wherein the agitation unit comprises:
    an agitation platform having the membrane placed thereon and receiving at least one antibody of the plurality of antibodies therewithin; and
    a platform maneuvering assembly operatively connected to the agitation platform, wherein the platform maneuvering assembly comprises:
        a connecting rod operatively connected to a bottom portion of the agitation platform;
        a crank connected to the connecting rod;
        a motor assembly connected to the crank, the motor assembly operates to rotate the crank thereby moving the connecting rod for facilitating agitation movements of the agitation platform, wherein the agitation movements assist interaction of the plurality of antibodies with the samples in the membrane.

9. The integrated system according to claim 8, wherein the agitation platform comprises at least one probing chamber, a probing chamber holds the membrane and the at least one antibody.

10. The integrated system according to claim 8 further comprises a base unit, the agitation platform is pivotally mounted on the base unit to facilitate the agitation movements.

11. The integrated system according to claim 8, wherein the supply unit comprises a plurality of tubes arranged in the modules holder, wherein each tube holds an antibody of the plurality of antibodies.

12. The integrated system according to claim 11, wherein the supply unit further comprises a pumping system connected to the plurality of tubes, the pumping system operates to supply an antibody from a tube of the plurality of tubes to the agitation platform.

13. The integrated system according to claim 8 further comprises:
    a plurality of storage units, wherein at least one storage unit comprises washing fluids; and
    a fluid pump system for delivering washing fluid into the agitation platform for washing the membrane.

14. The integrated system according to claim 13, wherein at least one storage unit of the plurality of storage units comprises the transfer buffer, wherein the fluid pump system is further configured to deliver the transfer buffer into the transfer unit.

15. The integrated system according to claim 14 further comprises:
- a plurality of supply tubes, wherein a supply tube of the plurality of supply tubes connects a storage unit of the plurality of storage units to the fluid pump system; and
- a plurality of tube holders, wherein a tube holder is clamped to the supply tube for holding the supply tube in a predefined position.

16. The integrated system according to claim 13, wherein the drying unit comprises:
- at least one membrane holder arranged within the drying chamber, a membrane holder having at least one slit configured to hold the membrane contacting two end portions of the membrane within the drying chamber; and
- an air supply unit for supplying air along the membrane for drying.

17. The integrated system according to claim 1 further comprises a control unit communicatively connected to a transfer unit, a probing unit and a drying unit, wherein the control unit controls the operation of the transfer unit, the probing unit and the drying unit.

18. A system for managing electro-blotting and blotting comprising:
- a modules holder comprising a transfer compartment, a probing compartment and a dryer compartment;
- a transfer unit arranged in the transfer compartment, the transfer unit receives at least one transfer sandwich holder, each transfer sandwich holder holding a transfer sandwich comprising a gel member and a membrane, wherein the transfer unit is configured to transfer samples from the gel member to the membrane;
- a probing unit arranged in the probing compartment, the probing unit receives the membrane there within, the membrane is exposed to a plurality of antibodies for binding with the samples in the membrane; and
- a drying unit arranged in the dryer compartment, the drying unit dries the membrane with hot air.

19. The system according to claim 18, wherein the transfer unit comprises:
- at least one sandwich slot for holding a transfer sandwich holder of the at least one transfer sandwich holder; and
- a plurality of electrodes for facilitating the transfer of samples from the gel member to the membrane in presence of a transfer buffer, wherein an electrode of the plurality of electrodes comprises:
  - a fastening unit for arranging the electrode within a sandwich slot of the at least one sandwich slot; and
  - at least one wire wounded around the electrode.

20. The system according to claim 18, wherein the probing unit comprises:
- an agitation unit for holding the membrane and capable of performing agitation operation for interacting the plurality of antibodies with samples in the membrane, wherein the agitation unit comprises:
  - an agitation platform having the membrane placed thereon and receiving the plurality of antibodies therewithin; and
  - a platform maneuvering assembly operatively connected to the agitation platform, wherein the platform maneuvering assembly comprises:
    - a connecting rod operatively connected to a bottom portion of the agitation platform;
    - a crank connected to the connecting rod;
    - a motor assembly connected to the crank, the motor assembly operates to rotate the crank thereby moving the connecting rod for facilitating agitation movements of the agitation platform, wherein the agitation movements assist interaction of the plurality of antibodies with the membrane; and
- a supply unit for supplying the plurality of antibodies into the agitation platform, wherein the supply unit comprises a plurality of tubes, wherein each tube holds an antibody of the plurality of antibodies.

21. The system according to claim 18, wherein the drying unit comprises:
- at least one membrane holder arranged within the drying chamber, a membrane holder having at least one slot configured to hold the membrane contacting two end portions of the membrane within the drying chamber; and
- an air supply unit for supplying air along the membrane for drying.

22. The system according to claim 18 further comprises a card holder having:
- a plurality of holder slots for holding at least one filter pad, at least one buffer pad, at least one membrane and at least one gel member; and
- at least one reservoir for holding fluids, wherein a reservoir of the at least one reservoir supplies a fluid to at least one holder slots of the plurality of holder slots.

* * * * *

UNITED STATES PATENT AND TRADEMARK OFFICE
CERTIFICATE OF CORRECTION

PATENT NO. : 9,945,810 B2
APPLICATION NO. : 15/038976
DATED : April 17, 2018
INVENTOR(S) : Urban Jonsson Axelsson et al.

It is certified that error appears in the above-identified patent and that said Letters Patent is hereby corrected as shown below:

In the Claims

At Column 18, Line 4, delete "e" and insert --the--.

At Column 18, Line 10, delete "fluffier" and insert --further--.

Signed and Sealed this
Nineteenth Day of June, 2018

Andrei Iancu
*Director of the United States Patent and Trademark Office*